US006776765B2

(12) United States Patent
Soukup et al.

(10) Patent No.: US 6,776,765 B2
(45) Date of Patent: Aug. 17, 2004

(54) STEERABLE STYLET

(75) Inventors: Thomas M. Soukup, Plymouth, MN (US); John D. Wright, Wyoming, MN (US); William Kuester, Blaine, MN (US); Patrick Haley, Elk River, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 351 days.

(21) Appl. No.: 09/934,245

(22) Filed: Aug. 21, 2001

(65) Prior Publication Data

US 2003/0040684 A1 Feb. 27, 2003

(51) Int. Cl.$^7$ .............................................. A61B 5/00
(52) U.S. Cl. ...................... 600/585; 600/435; 604/528; 604/95.01; 606/129
(58) Field of Search ........................... 600/433–435, 600/585, 462; 607/119, 122, 116; 606/41, 129; 604/95.01, 95.04, 95.05, 264, 523, 528

(56) References Cited

U.S. PATENT DOCUMENTS

| | | |
|---|---|---|
| 2,118,631 A | 5/1938 | Wappler |
| 3,802,440 A | 4/1974 | Salem et al. |
| 4,209,019 A | 6/1980 | Dutcher et al. |
| 4,215,703 A | 8/1980 | Willson |
| 4,271,845 A | 6/1981 | Chikashige et al. |
| 4,456,017 A | 6/1984 | Miles |
| 4,719,924 A | 1/1988 | Crittenden et al. |
| 4,757,827 A | 7/1988 | Buchbinder et al. |
| 4,822,345 A | 4/1989 | Danforth |
| 4,886,067 A | 12/1989 | Palermo |
| 5,060,660 A | 10/1991 | Gambale et al. |
| 5,282,478 A | 2/1994 | Fleischhaker, Jr. et al. |
| 5,304,131 A | 4/1994 | Paskar |
| 5,315,996 A | 5/1994 | Lundquist |
| 5,322,064 A | 6/1994 | Lundquist |

(List continued on next page.)

FOREIGN PATENT DOCUMENTS

WO   WO 00/22981   4/2000

OTHER PUBLICATIONS

*Medtronic Placer™ Model 6232 Steerable Stylet*, Premarket Notification document, Medtronic, Inc., 4 pgs.; Jun. 16, 2000.
*Medtronic Eupalamus Deflectable Stylet*, Premarket Notification document, Medtronic, Inc., 8 pgs.; Oct. 18, 2000.

(List continued on next page.)

*Primary Examiner*—Charles Marmor
(74) *Attorney, Agent, or Firm*—Fredrikson & Byron, P.A.

(57) ABSTRACT

A steerable stylet for use within a lumen of an intravascular device includes a stylet assembly and a handle. The stylet assembly has a distal end portion and a proximal end portion and includes a stylet wire having a lumen and a core wire positioned within the lumen with the distal end portion secured to the stylet wire proximate the distal end portion of the stylet wire. The handle includes a hand-held housing structure connected to one of the proximal end portion of the stylet wire or the core wire. In one embodiment, an adjustable tensioner is connected to the other of the proximal end portion of the stylet wire or the core wire to adjust a relative tension force applied between the stylet wire and the core wire. A tension limiter is arranged to limit the tension force to a limit force that is less than a breaking stress force of the stylet wire when the stylet wire is positioned within the lumen of the intravascular device.

59 Claims, 16 Drawing Sheets

U.S. PATENT DOCUMENTS

| | | |
|---|---|---|
| 5,327,906 A | 7/1994 | Fideler |
| 5,396,902 A | 3/1995 | Brennen et al. |
| 5,437,288 A | 8/1995 | Schwartz et al. |
| 5,439,006 A | 8/1995 | Brennen et al. |
| 5,441,483 A | 8/1995 | Avitall |
| 5,573,520 A | 11/1996 | Schwartz et al. |
| 5,605,162 A | 2/1997 | Mirzaee et al. |
| 5,605,543 A | 2/1997 | Swanson |
| 5,662,119 A | 9/1997 | Brennen et al. |
| 5,674,271 A | 10/1997 | Denker |
| 5,726,615 A | 3/1998 | Bloom |
| 5,743,876 A | 4/1998 | Swanson |
| 5,752,915 A | 5/1998 | Neubauer et al. |
| 5,758,656 A | 6/1998 | Schroeder |
| 5,820,591 A | 10/1998 | Thompson et al. |
| 5,824,031 A | 10/1998 | Cookston et al. |
| 5,833,632 A | 11/1998 | Jacobsen et al. |
| 5,851,203 A | 12/1998 | van Muiden |
| 5,873,842 A | 2/1999 | Brennan et al. |
| 5,916,178 A | 6/1999 | Noone et al. |
| 5,938,623 A | 8/1999 | Quiachon et al. |
| 5,957,903 A | 9/1999 | Mirzaee et al. |
| 6,004,279 A | 12/1999 | Crowley et al. |
| 6,017,319 A | 1/2000 | Jacobsen et al. |
| 6,027,462 A | 2/2000 | Greene et al. |
| 6,039,743 A | 3/2000 | Quiachon et al. |
| 6,048,339 A | 4/2000 | Zirps et al. |
| 6,059,739 A | 5/2000 | Baumann |
| 6,068,623 A | 5/2000 | Zadno-Azizi et al. |
| 6,132,390 A | 10/2000 | Cookston et al. |
| 6,183,420 B1 | 2/2001 | Douk et al. |
| 6,203,506 B1 | 3/2001 | Boström |
| 6,485,440 B1 * | 11/2002 | Gardeski .................... 600/585 |
| 6,607,496 B1 * | 8/2003 | Poor et al. ................. 600/585 |

OTHER PUBLICATIONS

Web site print-out: *New Implantation Tool, Steerable Stylet Clinical Assessment Study*, Fikru Maru, Joachim Kruetzer, Rolf Pieper, Peter Steen Hansen, Peter Zwicky, Mariette Schönbeck, Thomas Vesterlund, HeartWeb Organization, vol. 4, No. 1, Article No. 98110008, 8 pgs.; Nov. 1998.

* cited by examiner

STEERABLE STYLET

FIELD OF THE INVENTION

The present invention relates generally to the field of intravascular leads and catheters. More specifically, the present invention relates to steerable stylet for use in positioning such leads and catheters.

BACKGROUND OF THE INVENTION

Stylets and guidewires are used to control the manner in which intravascular leads and catheters are introduced into the veins or arteries of the body. Although both kinds of devices are often thought of as simply very small wires, the purpose and operation of stylets is significantly different as compared to guidewires.

Conventional intravascular procedures typically involve an initial step of introducing and routing a guidewire through a patient's vascular system to provide a rail or track along which additional intravascular devices may be introduced. Once a guidewire is in place, a sheath is routed over at least a portion of the guidewire to provide a larger opening into the vein or artery and sometimes to protect the inside walls of the vessels along the route of the guidewire. With the sheath in place, the guidewire may be removed or may remain in place as additional intravascular devices, such as intravascular leads and catheters, are introduced into the patient's vascular system.

To better accomplish the purpose of a guidewire providing a track along the patient's vascular system for other intravascular devices, it is desirable that the guidewire be extremely flexible and preferably have the ability to vary the flexibility of the distal tip and/or deflect the distal tip so as to aid in routing the guidewire through the patient's vascular system. U.S. Pat. Nos. 4,215,703, 4,456,017, 4,719,924, 4,757,827, 4,886,067 and 5,060,660 describe designs for guidewires that use an internal tensioning member or core wire to alter the characteristics of the non-expandable distal tip and/or to deflect the distal tip. U.S. Pat. Nos. 4,271,845 4,822,345, 5,605,162, 5,762,615, 5,851,203, 5,957,903 and 6,183,420 describe various designs for guidewires with adjustable stiffness by moving a core member axially within the guidewire. U.S. Pat. Nos. 5,938,623 and 6,039,743 describe a guidewire with adjustable stiffness that is controlled by running electricity through a memory metal wire tip. Flexibility of the guidewire has also been provided by gradually tapering some portion of the distal end as described in U.S. Pat. Nos. 5,851,203 and 5,916,178 or by changing materials at the end of the guidewire as described in U.S. Pat. Nos. 6,017,319 and 6,068,623. The flexibility of guidewires has also been enhanced by making cuts or slots in the distal region of the guidewire as shown in U.S. Pat. Nos. 3,802,440, 5,437,288, 5,605,543, 5,833,632, 6,004,279 and 6,017,319. Similar arrangements for increasing the flexibility of the catheter that is tracked over the guidewire are also described in U.S. Pat. Nos. 5,304,131, 5,315,996, 5,322,064, 5,441,483, 5,573,520, 5,743,876 and 6,048,339. Catheter arrangements capable of producing compound bends are described in U.S. Pat. Nos. 5,758,656 and 5,820,591.

In contrast to the guidewire that serves as a track over which other intravascular devices are routed, a stylet is used within an internal lumen of an intravascular device both to push that device through the vascular system and to steer the device as it is being pushed. Although some intravascular devices are designed to steer themselves using internal core wires, almost all leads, most catheters and some guidewires have an inner channel or lumen into which a stylet is inserted. In addition to pushing the intravascular device through the vascular system by engaging the distal end of the device, the stylet also serves to deflect the distal end of the intravascular device so as to steer the distal end through the vascular system. Unlike the lead, catheter or guidewire, which is highly flexible and floppy, the stylet must be stiffer and more rigid so as to enable the stylet to push the lead or catheter through the patient's vascular system. In addition, guidewires have diameters that are typically at least twice as large (0.030–0.040 inches) as the diameters of stylets (less than 0.016 inches) because guidewires are most often formed of a coiled wire, instead of a straight tubular wire.

Conventionally, stylets having different bends on the distal end are used at different points of advancing the lead or catheter to a desired location. For straight segments of a vessel a straight stylet is used, whereas a stylet with a curved distal tip is used to navigate the lead or catheter through a curved portion of a vessel. U.S. Pat. No. 2,118,631 shows an early stylet formed of coils of flat wire welded to plugs at both ends that could be bent by the physician into either a straight or curved configuration at its distal end prior to insertion into the lumen of a catheter or the like. U.S. Pat. Nos. 4,498,482 and 4,796,642 show early examples of solid wire stylets. While such conventional stylets can be used effectively in the hands of a skilled surgeon, the process can be complicated and time consuming. Implantation of a lead with a conventional stylet often involves multiple insertions and withdrawals of the stylet, with the surgeon adjusting the bend on the distal end so as to be able to continue to advance the stylet and lead into a desired position. One type of lead placement that is particularly complicated is the placement of a J-shaped lead in the atrial chamber. In this procedure, a straight stylet is used to advance the lead into the atrial chamber of the heart. Once there, a J-shaped stylet is used to force the lead to bend back on itself in order to be secured in a desired location in the atrium.

To overcome the problem of having to repeatedly insert and withdraw a stylet in order change the shape of the distal end, attempts have been made to develop a steerable stylet. In a steerable stylet an operator uses a handle at the proximal end of the stylet to control the direction of deflection of the distal tip of the stylet while it is in place in the lumen of the lead or catheter as it is moved along the veins or arteries. Typically, a steerable stylet is arranged as a stylet wire having a lumen within which a core wire is positioned with the distal ends of the two wires being attached. The handle is used to create a differential tension between the core wire and the stylet wire so as to deflect the distal end of the stylet as a result. Examples of such steerable stylets with deflectable tips are shown in U.S. Pat. Nos. 4,209,019, 5,396,902, 5,439,006, 5,662,119, 5,674,271, 5,824,031, 5,873,842, 6,027,462, 6,059,739, and 6,203,506. Other examples of steerable stylets can be found in PCT Publ. No. WO 00/22981 and publications describing the Placer™ steerable stylet and the Locator™ steerable stylet.

In U.S. Pat. No. 5,752,915, a steerable stylet uses an operating slide to retract a stylet sleeve that is not attached to the stylet wire so as to selectively expose a pre-bent distal portion of a stylet wire to deflect the distal end of an electrode lead. The handle of this stylet includes a spring for the purpose of enclosing the proximal end of the stylet wire in a tight brace to prevent buckling of the stylet wire due to friction between the stylet wire and the stylet sleeve as the stylet sleeve is retracted. In U.S. Pat. No. 5,327,906, a stress relief sleeve is provided at the junction of the stylet wire and a nose cone for the handle that allows the stylet to be removably mounted in the handle. A stop pin is also used to limit the rearward travel of a slide for the purpose of controlling the degree of curvature of the distal end of the stylet by using the stop pin to change the length of the slide. In U.S. Pat. No. 6,132,390, a conical tip is also provided to minimize stress on the stylet. A flexible plastic or polymeric jacket is disposed over the stylet wire to prevent kinking or catastrophic inelastic failure of the distal tip under a radial load.

While the advantages of a steerable stylet are apparent, none of the existing designs for steerable stylets has achieved widespread acceptance. One of the principle challenges in designing an effective steerable stylet is creating a robust design that enables a large curvature of the distal end, preferably more than 120° so as to accommodate placement of J-shaped leads or alternatively creating sigmoidal or compound bends, while at the same time providing the flexure strength to permit repeated bending of the stylet without fracture or breaking. Unlike guidewires or catheters, these design considerations must be developed to operate under conditions where the stylet is within and constrained by the lumen of the lead or catheter that is being implanted. It would be desirable to provide a steerable stylet that could overcome these challenges and provide a robust design capable of large or compound curvatures that safely allows for repeated bending of the stylet without fracture or breaking.

SUMMARY OF THE INVENTION

The present invention provides a steerable stylet for use within a lumen of an intravascular device. The stylet includes a stylet assembly and a handle. The stylet assembly has a distal end portion and a proximal end portion and includes a tubular stylet wire having a lumen and a core wire positioned within the lumen with the distal end portion secured to the stylet wire proximate the distal end portion of the stylet wire. Unlike a conventional guidewire, the stylet wire has diameter of less than 0.016 inches and a beam strength of at least 0.005 lbf as measured by the ASTM E855-90 3-point bend test. The core wire has a distal end portion and a proximal end portion and is positioned within the lumen of the stylet wire with the distal end portion secured to the stylet wire proximate the distal end portion of the stylet wire. The handle includes a hand-held housing structure connected to one of the proximal end portion of the stylet wire or the core wire. In one embodiment, an adjustable tensioner is connected to the other of the proximal end portion of the stylet wire or the core wire to adjust a relative tension force applied between the stylet wire and the core wire. A tension limiter is arranged to limit the tension force to a limit force that is less than a breaking stress force of the stylet wire when the stylet wire is positioned within the lumen of the intravascular device. In another embodiment, a plurality of notches are defined in one or more regions of the distal portion of the tubular stylet wire to aid in the safe and effective creation of large and/or compound curves. Preferably, the core wire is secured within the tubular stylet wire without heating either wire so as to prevent any annealing of the materials that would decrease the tensile strength of the distal end portion of the stylet.

By limiting the tension force that can be applied between the core wire and the stylet wire to a force that is less than the breaking stress force of the stylet wire, the present invention prevents the stylet wire from failing as a result of an excessive stress force. This prevents an operator from overexerting the stylet wire by attempting to deflect the stylet in a situation where the intravascular device cannot be deflected, such as for example within a blood vessel. Unlike a design that provides for a fixed dimensional travel of the adjustable tensioner, the present invention provides for a floating or variable amount of travel up to a maximum deflection force. As a result, the stylet may be repeatedly deflected numerous times without causing either a stress or fatigue failure of the stylet wire. In one embodiment, the steerable stylet of the present invention is designed for implantation of cardiac J-leads and can be deflected up to a maximum deflection of at least 180° from an original position of the stylet wire and the deflections can be repeated at least fifty times without inducing stress or fatigue failure in the stylet wire. In another embodiment, the steerable stylet of the present invention is designed for use in neurological applications and can be deflected up to a maximum of 90° and can also be configured to create compound curves.

In a preferred embodiment, a series of at least ten notches are defined along a distal region of the stylet wire to prevent the stresses induced in the distal region of the stylet wire from kinking or bending the stylet when the distal end portion of the stylet is deflected by an operator. Preferably, the series of notches in the distal region includes at least a portion of the notches that have a progressively decreasing depth distally to proximally along the series. More preferably, the portion of the notches having a progressively decreasing depth has a constant decrease in depth between adjacent notches. In this embodiment, the distal region is preferably defined beginning between 0.050 inches and 1.000 inches proximal to the distal end of the stylet wire. Preferably, there are at least twenty-five notches of between 0.005 inches and 0.015 inches longitudinal width with a spacing between adjacent notches of between 0.010 inches and 0.050 inches and a depth of at least ten of the most distal notches of said series being approximately equal to a radius of the stylet wire minus a wall thickness of the stylet wire. In an alternate embodiment, more than one series of notches are defined in the distal region of the stylet wire to create compound curves, including curves oriented in two different planes. Preferably, the spacing and dimensions of the notches are different between the different series so as to stage the sequence in which each region associated with a given series of notches will induce a curve in response to tension on the core wire.

In a preferred embodiment, the proximal end portion of the core wire is fixedly connected to the adjustable tensioner and the tension limiter has a first end portion fixedly connected to the housing structure of the handle and a second end portion operably connected to the adjustable tensioner. Preferably, the breaking stress force of the stylet wire is at least six pounds and the limit force of the tension limiter is less than four pounds. In one embodiment, the tension limiter is a constant force spring. In another embodiment, the tension limiter is an elastomer member with a maximum compressive retention force less than the breaking stress force of the stylet wire.

Preferably, the core wire is secured within the tubular stylet wire without heating either wire so as to prevent any annealing of the materials that would decrease the tensile strength of the distal end portion of the stylet. In one embodiment, the core wire is taper ground to provide a smaller diameter core shaft while leaving a bulbous distal end having a diameter substantially equal to an outer diameter of the tubular stylet wire. The core wire is slide into the lumen of the tubular stylet wire and the bulbous distal end of the core wire is secured in place using adhesives together with a chamfered fit. By avoiding the use of heat for welding or thermal expansive fits, the core wire and stylet wire are not annealed and the corresponding decrease in tensile strength of the wires (to about 60% of their original tensile strength) is not encountered.

In one embodiment, the handle includes a mechanism for providing tactile psuedo-feedback to an operator that is generally indicative of the relative tension force without directly engaging the tension limiter. In another embodiment, the beam strength of the stylet wire is preferably about 0.010 lbf so as to be sufficient to cause the stylet wire to return to at least an original position as the relative tension force is removed from the stylet wire and preferably to an angle beyond its original position.

DETAILED DESCRIPTION OF A PREFERRED EMBODIMENT

The present invention is directed to a steerable stylet 20 for use in various intravascular medical procedures, such as cardiac catheter procedures and neurological procedures. Although the present invention will be described with respect to embodiments designed specifically for cardiac and neurological procedures, it will be understood that a steerable stylet 20 in accordance with the present invention may be used to advance and steer any kind of intravascular device 50 through the vascular system of a patient to a desired treatment location.

Figure 1:
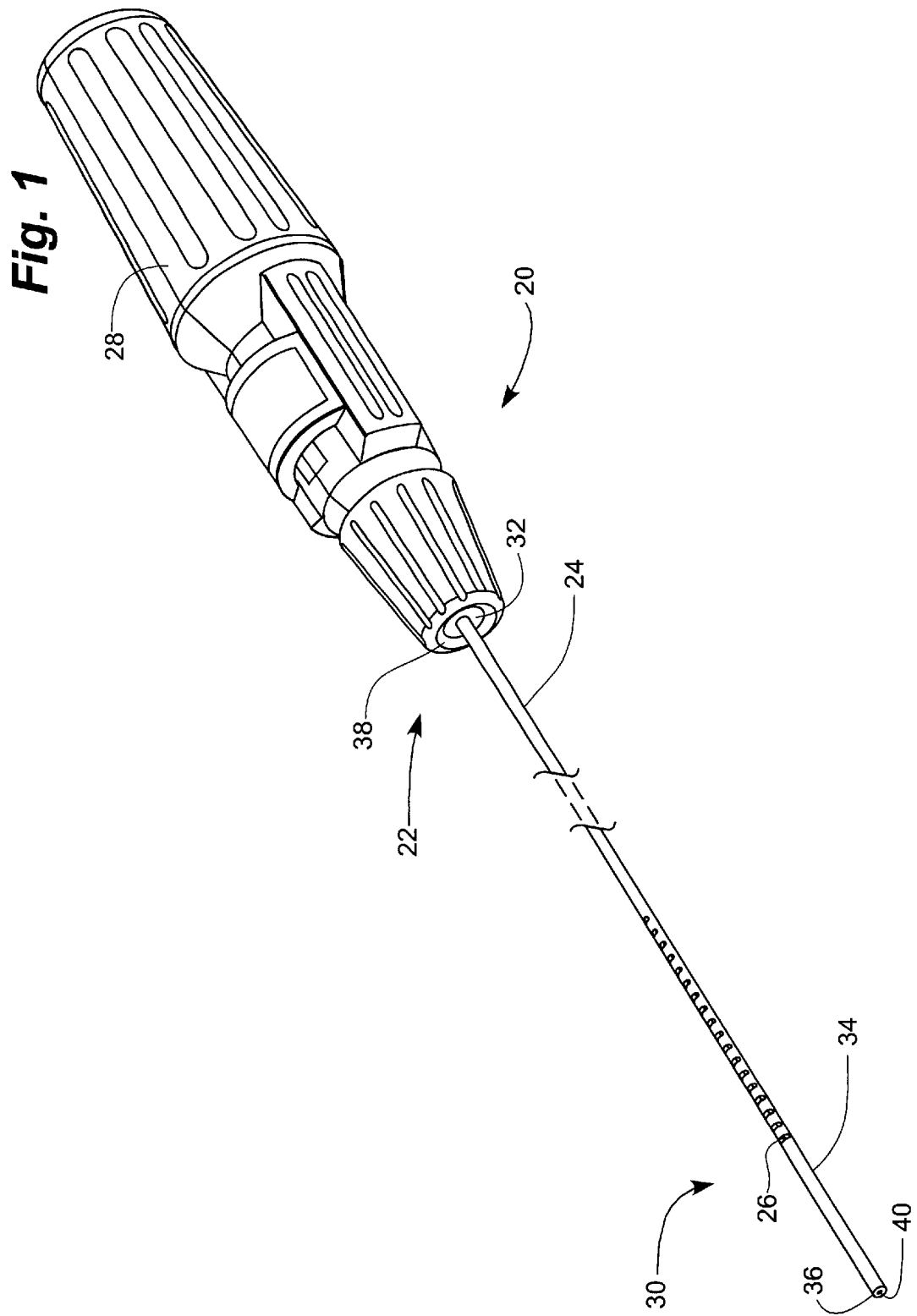
FIG. 1 is a perspective view illustrating the steerable stylet and manipulative handle assembly of the present invention.

Referring to FIG. 1, a steerable stylet 20 in accordance with the present invention broadly comprises a stylet assembly 22 that includes a stylet wire 24, a core wire 26, and a manipulative handle 28. For purposes of describing the present invention, the stylet assembly 22 includes a distal end portion 30 that can be selectively deflected by an operator through operation of the manipulative handle 28 operably connected to a proximal end portion 32 of the stylet assembly 22. It will be understood that the terms distal end portion and proximal end portion are used in the present invention to mean the longitudinal end as well as a portion proximate the longitudinal end and extending longitudinally back from the longitudinal end.

The stylet assembly 22 is preferably a multiple component arrangement that includes at least the stylet wire 24 having at least one lumen 34 defined therein with the core wire 26, sometimes referred to as a pull wire, positioned in the lumen 34. The distal end portion 36 of the stylet wire is fixedly attached to the distal end portion 40 of the core wire. Stylet wire 24 is preferably 300 series stainless steel tubing that may be either high tensile or low tensile. Core wire 26 is preferably 300 series stainless steel solid core wire that is preferably high tensile. Alternatively, stylet wire 24 and core wire 26 can be made of other metal alloys, such as nickel-titanium, or have a portion of each wire created from different material combinations (e.g., distal end portion 36 made from nickel-titanium and proximal end portion 32 made from stainless steel). Alternatively, core wire 26 could be made of other metal alloys or of a filament material sufficient strong enough to transmit the relative tension force (as will be described) without breaking. It should be noted that if the stylet wire 24 is welded to the core wire 26 at the distal end portions 36, 40, one or both of the wires may be annealed in the welding process.

Stylet wire 24 has an outer diameter of less than 0.016 inches and a beam strength of at least 0.005 lbf and preferably about 0.010 lbf as measured by the ASTM E855-90 3-point bend test, the specification of which is hereby incorporated by reference. In contrast, conventional floppy tip guidewires of the same relative size have beam strengths of less than 0.0025 lbf as measured by the ASTM E855-90 3-point bend test and more typically have beam strengths of only about 0.001 lbf. In one embodiment, stylet wire 24 has an inner diameter of 0.008 inches and core wire 26 has an outer diameter of 0.007 inches providing approximately 0.0005 inches clearance within the lumen 34. The outer diameter of less than 0.016 inches and beam strength of at least 0.005 lbf effectively permit stylet assembly 22 to be used as a stylet for insertion into a lumen of an intravascular device 50, as shown for example in FIGS. 14 and 15. Preferably, stylet wire 24 has a single lumen 34 to permit the outer diameter to be as small as possible while still providing sufficient strength so as to meet the beam strength requirements. Alternatively, stylet wire 24 could have multiple lumens although for current wire technology the number and size of the lumens will certainly impact on the beam strength and outer diameter limitations required by the present invention. In another embodiment, the lumen 34 in which core wire 26 is located could be defined partially or completely external to a solid stylet wire 24 by use of collars or rings attached to the exterior of the solid wire, for example, or by providing slots or openings in the lumen 34 of a tubular wire to allow core wire 26 to extend beyond the outer diameter of stylet wire 24 when a relative tension force is applied between stylet wire 24 and core wire 26.

The distal end portions 36 and 40 of the stylet wire 24 and the core wire 26 are preferably fixedly secured to one another without heating either wire so as to prevent any annealing of the materials that would decrease the tensile strength of the distal end portion of the stylet, such as by making a mechanical and/or adhesive connection or by crimping. Alternatively, the distal end portions 36 and 40 may be operably attached to one another by welding or soldering, or any combination of these techniques as long as the bond between the stylet wire 24 and the core wire 26 is at least as strong, and preferably stronger, than the materials of the wires themselves. In one embodiment, the longitudinal ends or tips of distal end portions 36 and 40 are secured together. Alternatively, the longitudinal tip of distal end portion 40 could be secured in the distal end portion 36 at a location other than the longitudinal end or tip that is proximate to the longitudinal tip.

Figure 12:
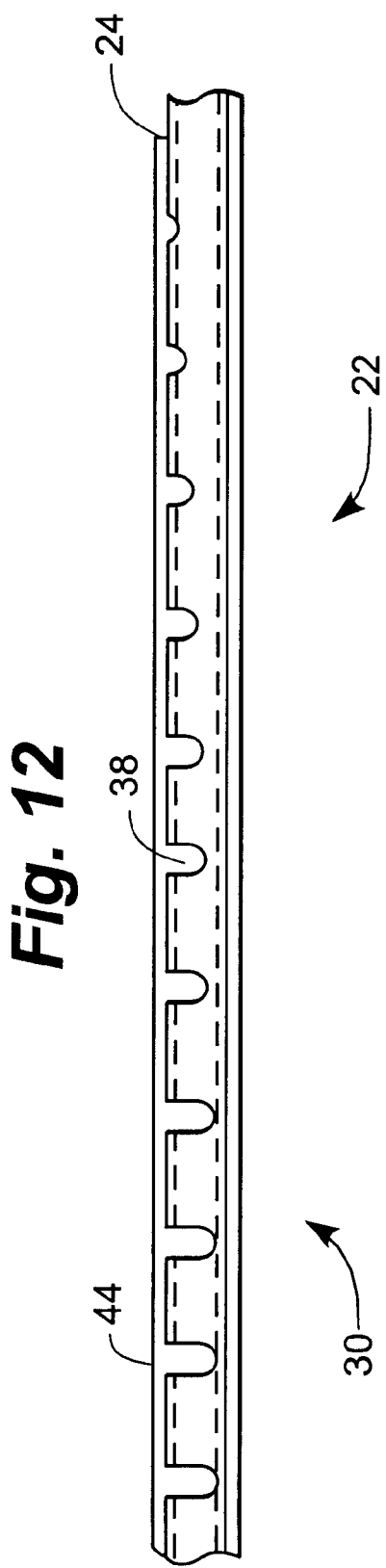
FIG. 12 is a detail of the notches in the distal portion of the stylet wire.

In one embodiment as shown in FIG. 12, stylet assembly 22 also includes a polymeric sheath 44 surrounding at least the distal end portion 30 of stylet assembly 22. The polymeric sheath, 44 is preferably a polyimide material. Alternatively, a Teflon® or Kapton® tubing material may be used. The polymeric sheath 44 is particularly suited for an embodiment of the steerable stylet 20 intended for cardiac-related uses where the vessels are somewhat larger and the intravascular devices 50 tend to have larger inner diameters. The polymeric sheath 44 serves to protect the stylet assembly 22 from body fluids and also can reduce sliding friction between the distal end portion 30 of stylet assembly 22 and the lumen of intravascular device 50. In a preferred embodiment for cardiac-related uses, the stylet assembly 22, including the polymeric sheath 44, has an outer diameter of 0.015 inches. In an alternative embodiment intended for neurological uses where smaller vessels are typically involved and the intravascular devices 50 tend to have lumens smaller inner diameters, the polymeric sheath 44 is not included and the stylet assembly 22 has an outer diameter of 0.013 inches. It will be understood that polymeric sheath 44 preferably extends at least over a distal region 46 in which a number of notches 48 are defined as will be described in connection with the description of FIG. 12. Alternatively, polymeric sheath 44 can extend over substantially the entire length of stylet wire 24.

It will be realized that a variety of treatments for constructing the distal end portion 30 of stylet assembly 22 can be utilized, depending upon the particular configuration and desired operation of the stylet assembly 22 within the intravascular device. For example, a ball, tube, or coiled spring could be added to the distal end portion 30 of the stylet assembly 22. Alternatively, distal end portion 30 could include a structure designed to engage a distal portion of the intravascular device 50, such as a flat driver structure or the like for extending and retracting a helical anchor coil located on the distal end portion of the intravascular device 50.

Figure 2:
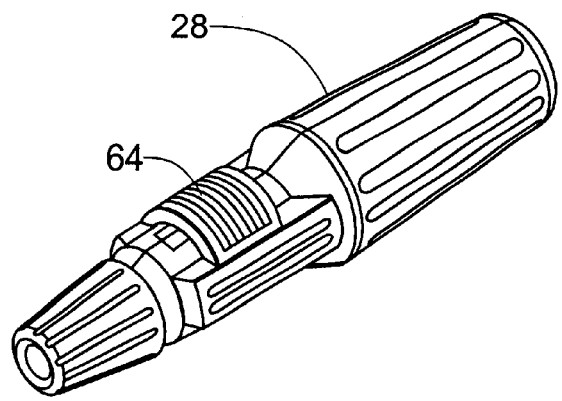
FIG. 2 is a perspective view of the first embodiment of the manipulative handle of the present invention in which the manipulation is controlled by sliding a thumb plate along the top of the handle.
Figure 3:
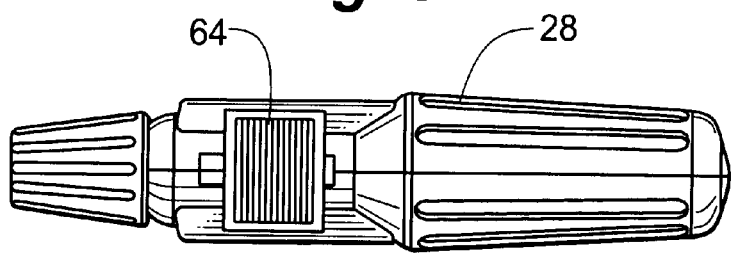
FIG. 3 is a top view of the embodiment shown in FIG. 2.
Figure 4:
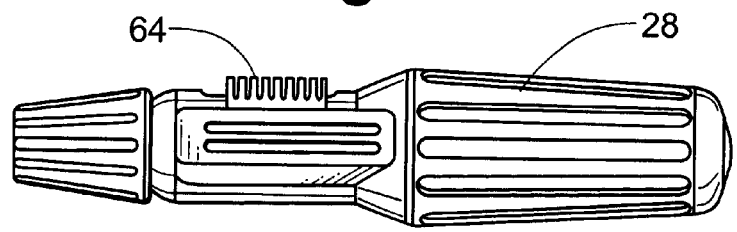
FIG. 4 is a side view of the embodiment shown in FIG. 2.
Figure 5:
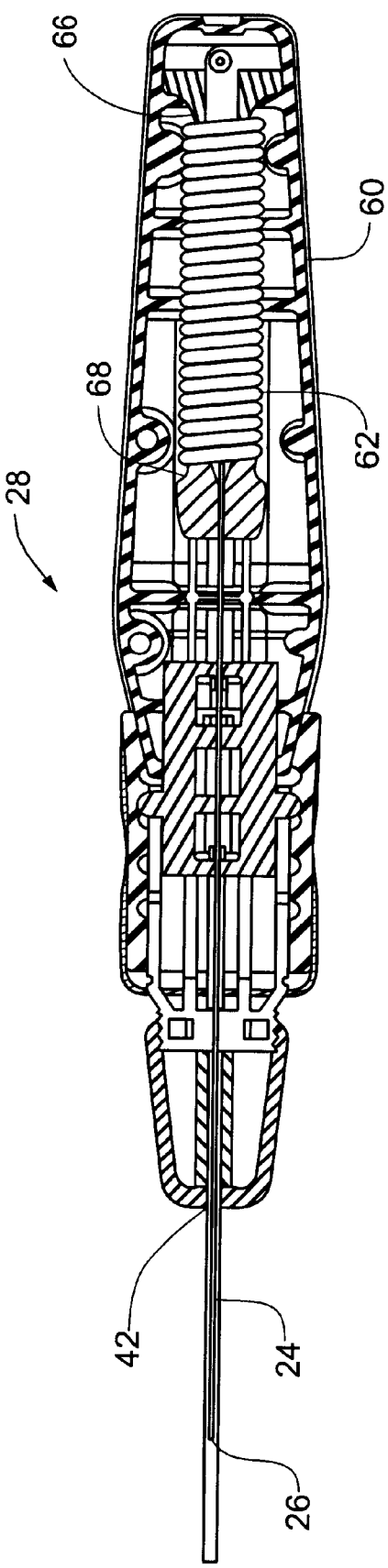
FIG. 5 is a longitudinal cross-section of the embodiment shown in FIG. 2.

FIG. 2 shows one embodiment of the manipulative handle 28. FIG. 5 presents a cross-section of the manipulative handle 28. The manipulative handle 28 comprises a housing 60, a tension limiting assembly 62, and an adjustable tensioner mechanism 64. In the embodiment shown in FIGS. 2 and 5, the adjustable tensioner mechanism 64 is a sliding mechanism and the tension limiting assembly 62 is a spring. The proximal end portion 42 of the core wire 26 is fixedly connected to the housing structure 60. The proximal end portion 38 of the stylet wire 24 is fixedly connected to the sliding mechanism 64. The tension limiting spring 62 has a first end portion 66 fixedly connected to the housing structure 60 and a second end portion 68 that is operably connected to the sliding mechanism 64. When the stylet handle 28 is activated by moving the sliding mechanism 64 in a distal direction, the stylet wire 24 moves distally, but the core wire 26 is restricted from moving, thus creating a relative tension force separating the core wire 26 from the stylet wire 24. In the event that that activated handle 28 is operated to exert a relative tension force of more than about four lbs. of force, the safety feature of the tension limiting spring 62 starts to open and restricts any further load build-up of force on the proximal end portion 32 of the stylet assembly 22, other than the constant force of the tension limiting spring 62 being extended.

Figure 16:
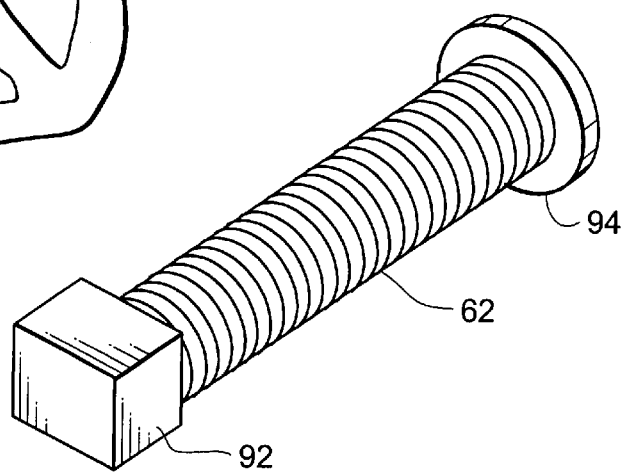
FIGS. 16 and 17 are isometric views of alternate embodiments of the tension limiting member.
Figure 17:
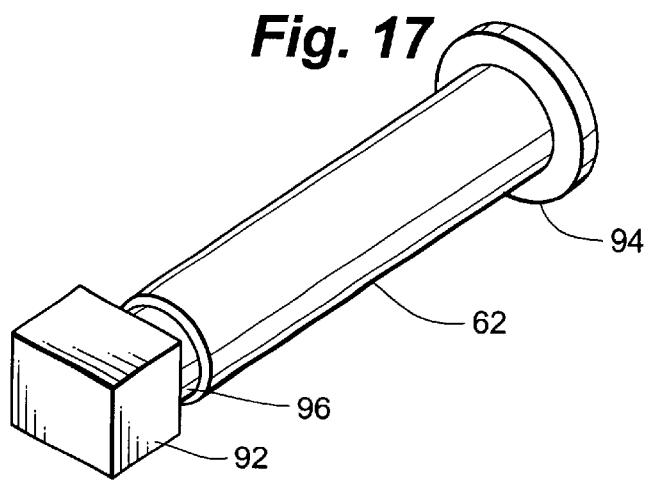

It will be appreciated that numerous combinations of operable connections among the proximal end portion 38 and 42 with the housing 60, adjusting mechanism 64 and tension limiting member 62 can be arranged to provide for a relative tension force that separates the core wire 26 from the stylet wire 24. For example, the core wire 26 could be coupled to the sliding mechanism 64 instead of the stylet wire 24, with the stylet wire 24 secured to the housing 60. Alternatively, one or the other of the stylet wire 24 or core wire 26 could be secured to the tension limiting member 62 with the other operably coupled to the adjusting mechanism 64. It will also be seen that the adjusting mechanism 64 can be made to operate in any number of arrangements, with the relative tension force created by a distal movement of the adjusting mechanism 64 or, alternatively, by a proximal movement of the adjusting mechanism 64. The tension limiting spring 62 can be arranged to operate in either compression or tension modes, depending upon the configuration of the other connections of the proximal end portions 38 and 42 of the stylet wire 24 and core wire 26 and the arrangements of the adjusting mechanism 64. Multiple adjusting mechanisms 64 can be arranged so as to provide, for example, for a course adjustment with a first mechanism and a fine adjustment with a second mechanism. FIGS. 16 and 17 show two different embodiments of tension limiting member 62. A first embodiment as shown in FIG. 16 in which tension limiting member 62 is a coil spring that is attached at each end to an engagement structure 92, 94 for engaging the tension limiting member 62 within place in the handle 60. FIG. 17 shows a second embodiment in which tension limiting member 62 is a tubular elastomeric material surrounding a compressible piston arrangement 96. It will be apparent that numerous other arrangements and configurations of the tension limiting member and the engagement structures could be used to accomplish the purpose of limiting the force applied to the stylet wire 24.

Figure 18:
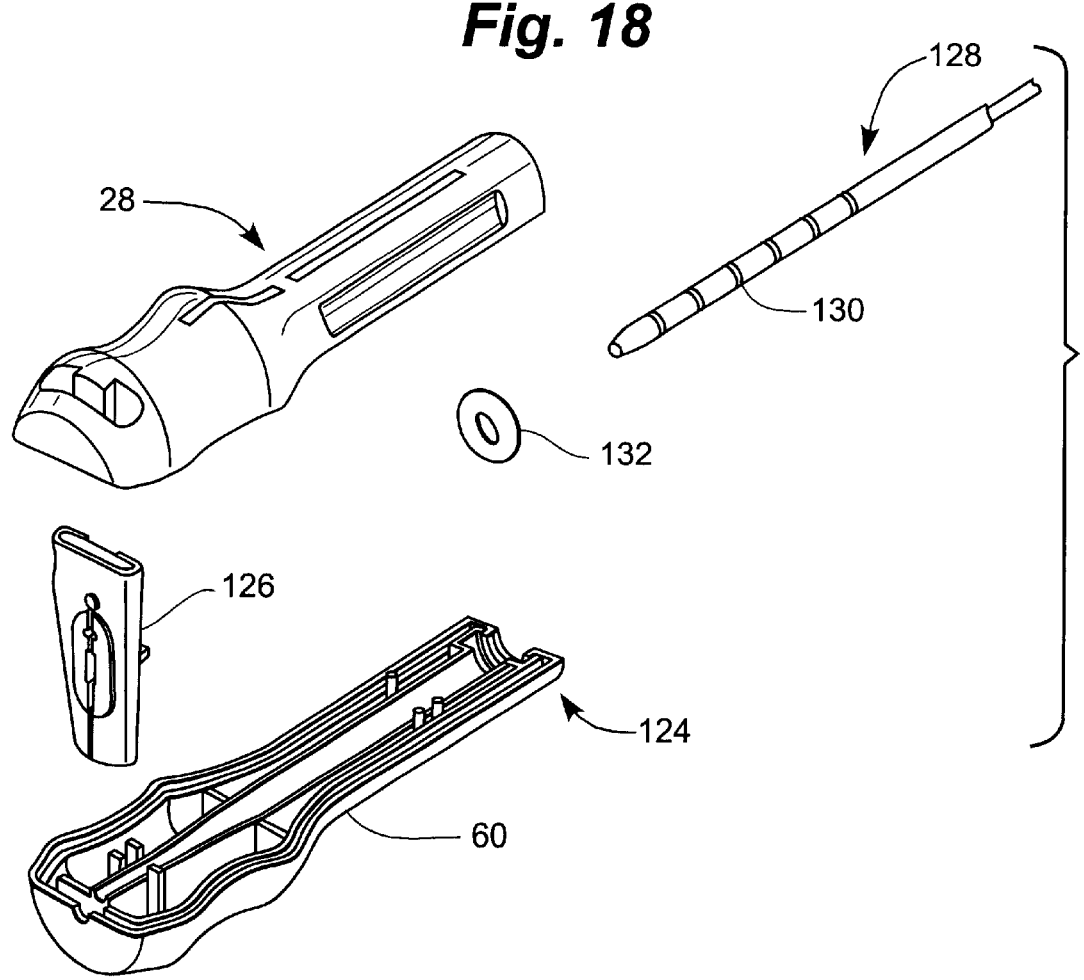
FIGS. 18 and 19 are exploded views of alternate embodiments of the front portion of the handle.

FIG. 18 presents one embodiment of a lead locking mechanism 124 that allows the manipulative handle 28 to be placed at multiple locations along the length of the proximal end of the lead 128. The lead locking mechanism 124 utilizes a lead clip 126 that secures the proximal end of the lead 128 to the housing 60 by gripping grooves 130 in the proximal end of the lead 128. The proximal end of the lead 128 feeds through a spacer 132 at the distal end of the manipulative handle 28 that keeps the proximal end of the lead 128 centered within the manipulative handle 28.

Figure 19:
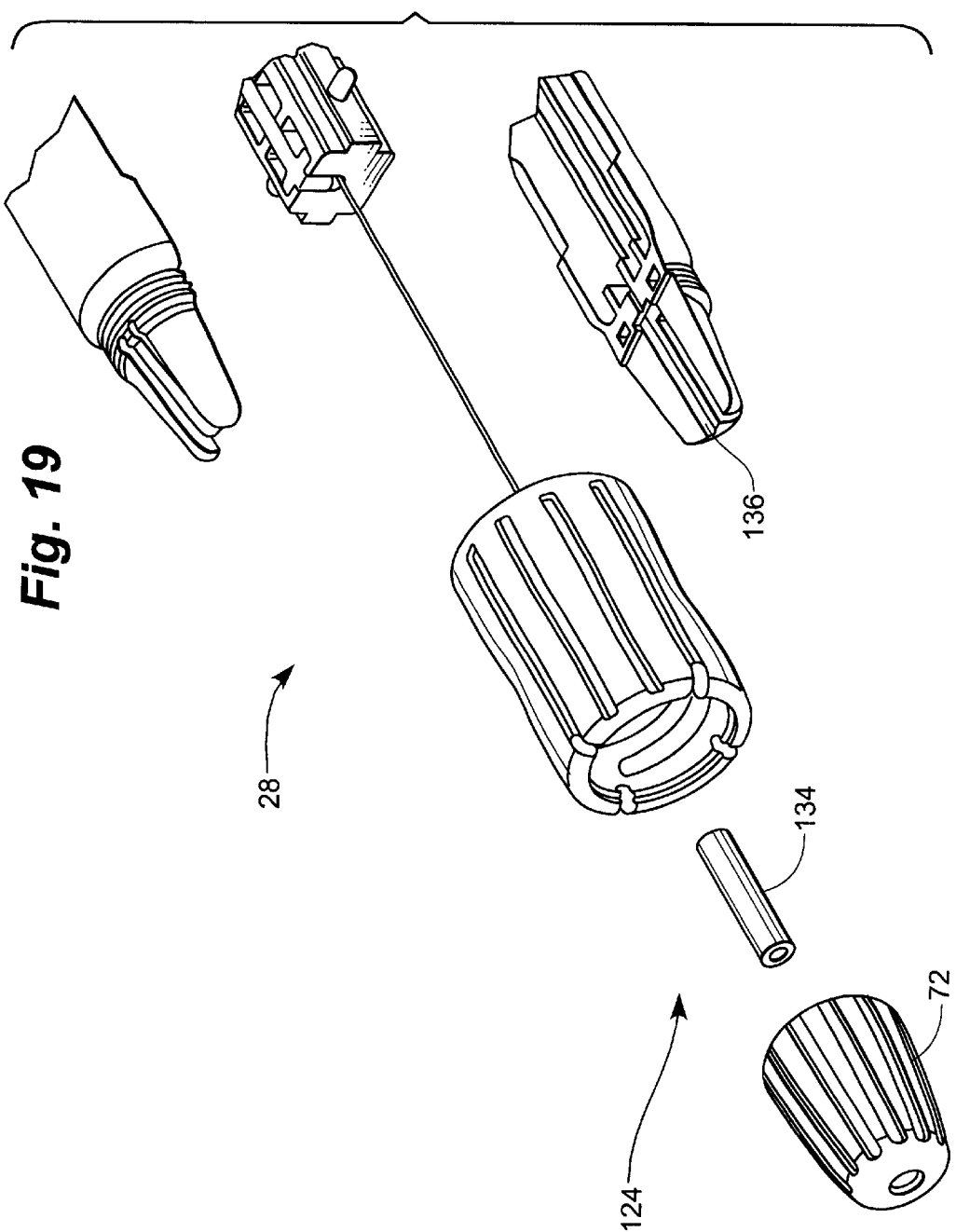

FIG. 19 presents another embodiment of the lead lock locking mechanism 124 where the proximal end of the lead 128 is threaded through a gland 134 that is in turn secured within a slot 136 at the proximal end of the manipulative handle 28. Twisting the rear portion 72 of the manipulative handle 28 provides compressive force to the gland 134, which secures the proximal end of the lead 128 within the manipulative handle 28.

Figure 20:
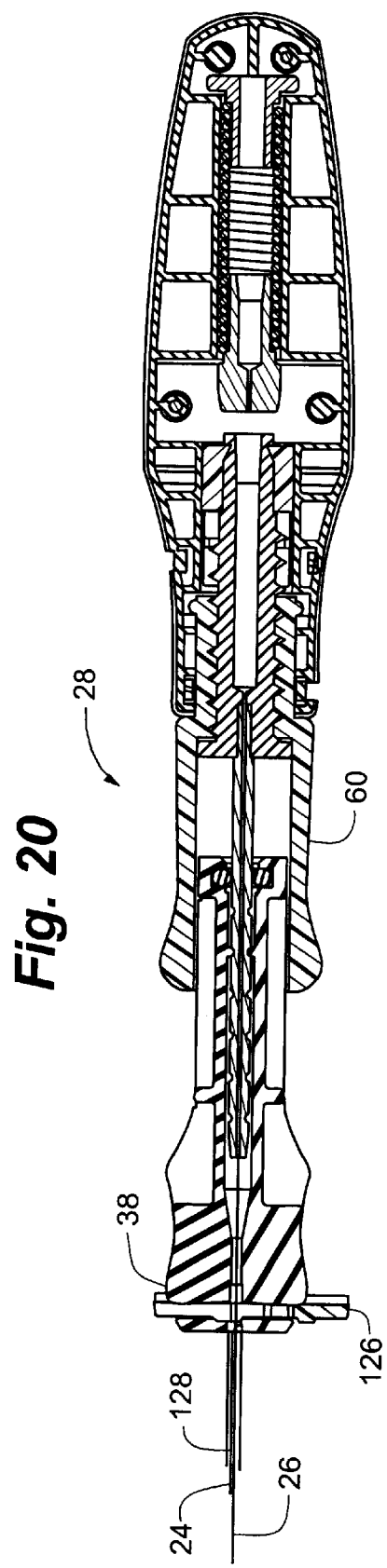
FIG. 20 is a cross-section view of an alternate embodiment of the handle having an adjustable front portion.

FIG. 20 shows an embodiment of the manipulative handle 28 that accommodates variations in stylet wire 24 and core wire 26 lengths. In this embodiment, the lead clip 126 is at the distal end 39 of the manipulative handle 28 and secures the proximal end of the lead 128 within the manipulative handle 28. The distal end 39 of the manipulative handle 28 may be moved toward or away from the housing 60 to accommodate different lengths of stylet wire 24 or core wire 26.

Figure 21:
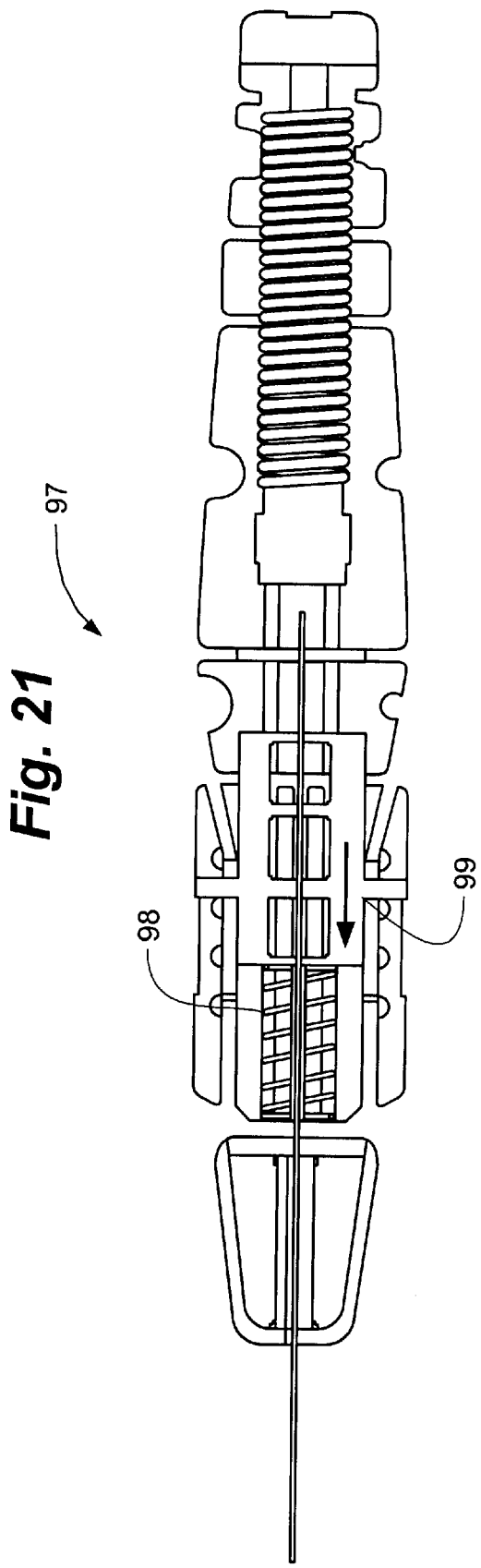
FIG. 21 is a cross-section view of an embodiment of the handle incorporating a tactile psuedo-feedback mechanism.

With reference to FIG. 21, one embodiment of the handle assembly 28 is provided with a tactile psuedo-feedback mechanism 97. Although a feedback mechanism could be provided which directly engaged the tension limiting member of the preferred embodiment, this would tend to complicate the design and introduce additional forces that would need to be accounted for in the design of the tension limiting member arrangement. Instead, this embodiment utilizes a compression spring 98 together with an engaging end 99 of sliding mechanism 64 positioned in the front portion of handle assembly 60. As the sliding mechanism 64 is operated to increase actual relative tension between the stylet wire 24 and the core wire 26, the engaging end 99 of the sliding mechanism 64 compresses the compression spring 98, thereby creating an increasing load on the sliding mechanism 64 that can be sensed by an operator during operation of the device as an increasing resistance to the ability to move sliding mechanism 64 forward. Preferably, the compression spring 98 is selected to provide a tactile feedback of increasing force that is similar in character to the actual force curve characteristics that occur for the particular stylet assembly 22. Preferably, the feedback spring 98 operates in a range that provides a feedback force of 0–2 lb. It will be understood that the force of feedback spring 98 can be scaled to operate in varying ranges based on the mechanical properties of the stylet 20 and the desired feedback for the operator. As with the actual tension limiting member 64, it will be recognized that numerous combinations and arrangements can be utilized to accomplish the desired effect of psuedo-feedback mechanism 97.

Figure 13:
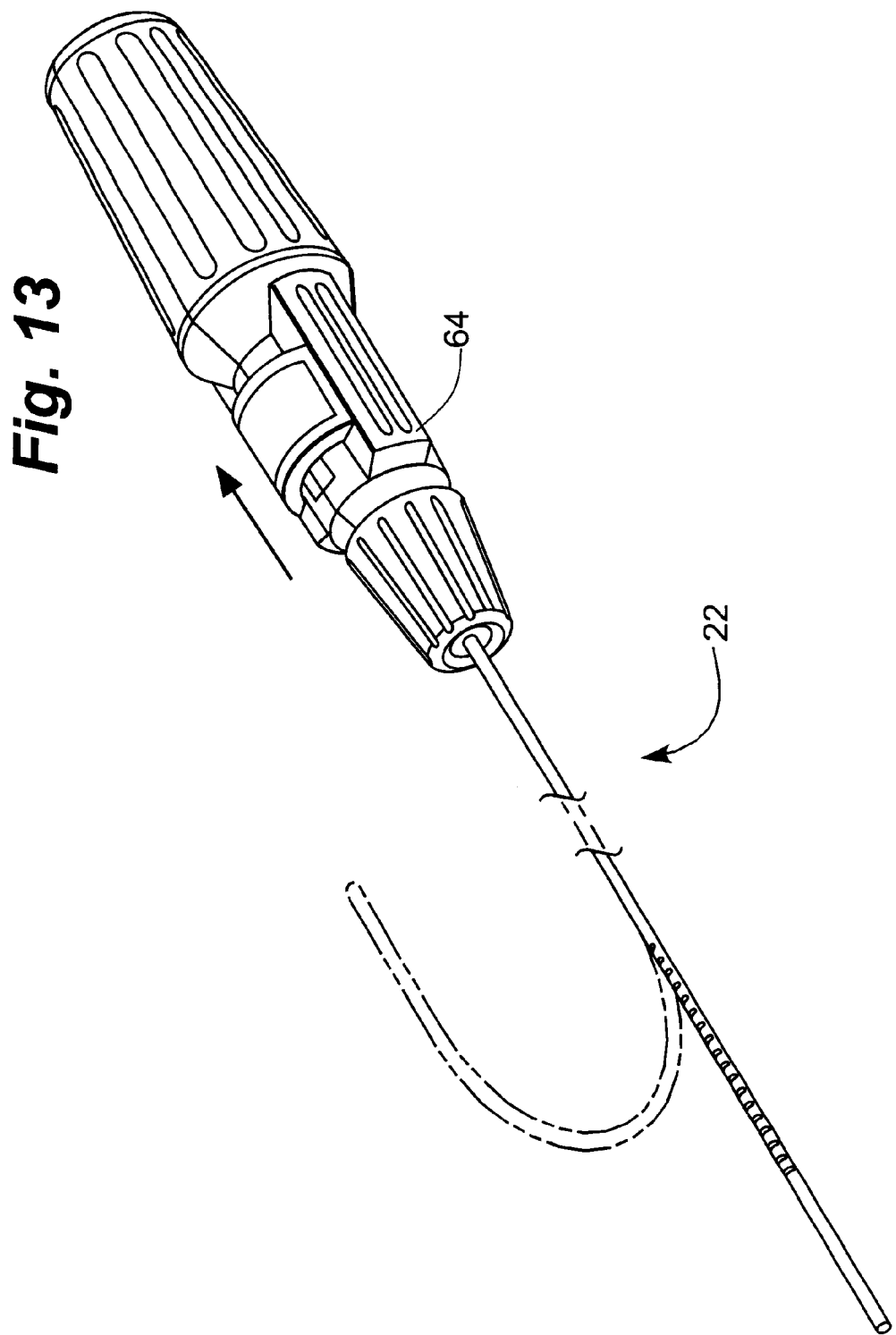
FIG. 13 is an illustration of the curvature imparted upon the stylet wire by manipulation of the handle in accordance with the teachings of the present invention.
Figure 14:
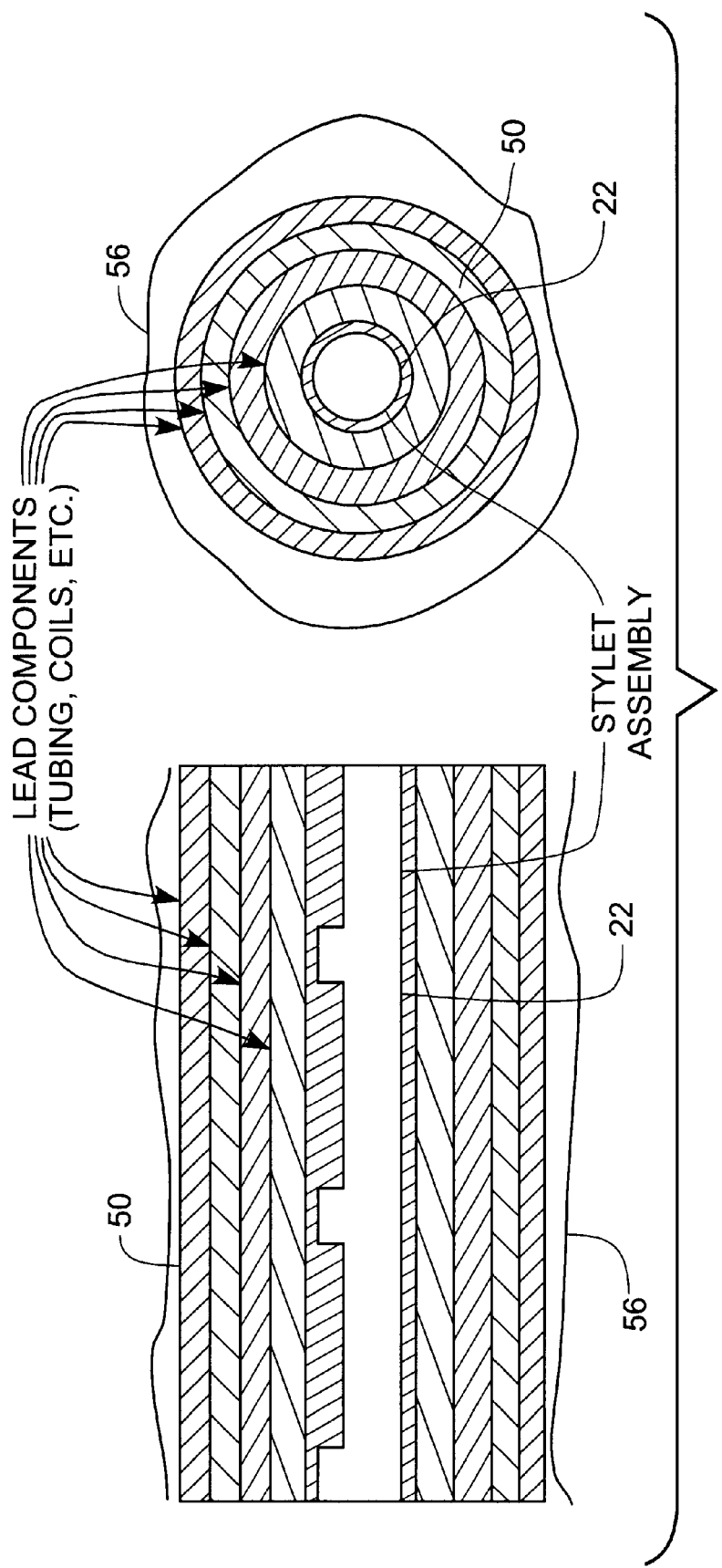
FIG. 14 provides cross-sections of a vein containing a steerable stylet within a medical lead.
Figure 15:
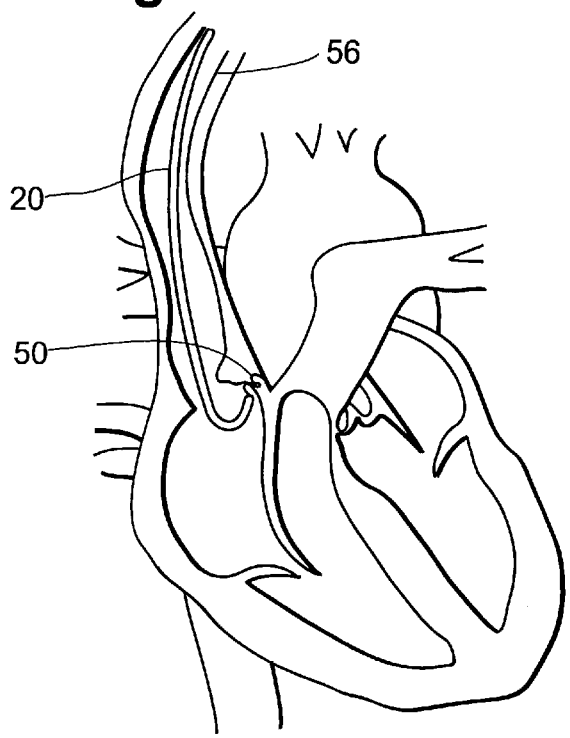
FIG. 15 is a cross-sectional view of the right atrium of a patient's heart containing a steerable stylet within a medical lead.

In an embodiment directed to cardiac applications, increasing the relative tension force between the stylet wire 24 and the core wire 26 causes the distal portion 30 of the stylet assembly 22 to bend until it ultimately forms a J-shape as illustrated in FIG. 13. The amount of curvature of the stylet wire 24 can be increased and decreased as necessary to traverse a body lumen or position the intravascular device 50 in a desired location. The curve of the J-shape that the distal portion 40 of stylet assembly 22 can assume when the sliding mechanism 64 is activated is preferably at least 180° and up to a 190° bend in a radius of less than 0.8" in response to a relative tension of about 3.5 lbs. FIG. 15 illustrates how the steerable stylet 20 of the present invention can be bent to allow for precise placement of a medical device such as a cardiac lead 50 in a patient's right atrium. FIG. 14 illustrates the stylet assembly 22 of the present invention within a medical lead 50 inside of a patient's vascular system 56.

Modeling of the stress levels at the distal end of the stylet wire have indicated that high stress levels are reached early on when bending of the distal region first occurs, remain relatively constant through the bending function, and then rise again when the maximum design radius is achieved. The actual stress is a combination of load stress when the core wire applies force to the stylet wire and beam stress while the stylet assembly is passing through the bend radius.

To insure that the stylet 20 and intravascular device 50 effectively return to an original or home position, the steerable stylet 20 of a preferred embodiment arcs up to 15° in an opposite direction from the J-shape when the relative tension force is removed between the stylet wire 24 and the core wire 26. Preferably, this counter-arcing is created due to the beam strength of the stylet wire 24. The counter-arcing overshoots the neutral home position after which the home position is obtained as the stylet wire relaxes. As a result, the steerable stylet 20 is more likely to ultimately return to a neutral home position after being repeatedly flexed.

Figure 6:
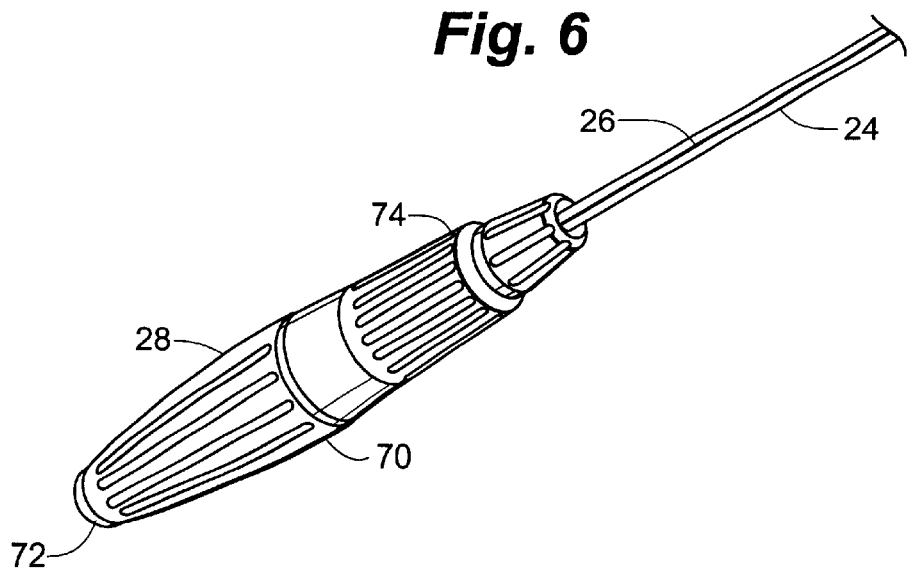
FIG. 6 is a side view of an additional embodiment of the manipulative handle of the present invention in which the manipulation is affected through turning a portion of the handle.
Figure 7:
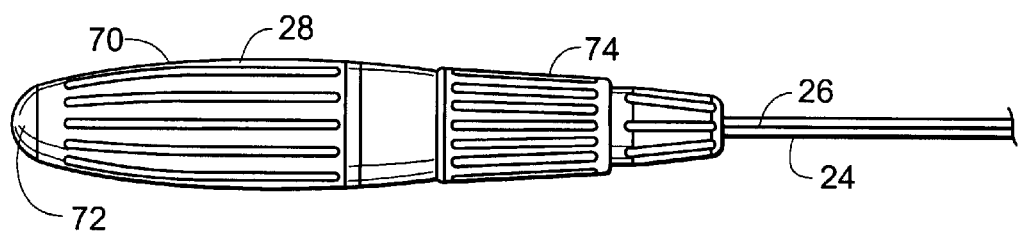
FIG. 7 is a top view of the embodiment shown in FIG. 6.

FIGS. 6 and 7 present a perspective and side view, respectively, of another embodiment of the manipulative handle 28 of the present invention in which relative tension force is applied to the stylet assembly 22 by twisting a rear portion 72 of the handle housing 70 in relation to the front portion 74 of the handle 70. Alternatively, a rotatable collar or similar arrangement could be mounted on the handle 70 to accomplish the same function. The rotational force is translated by a screw or other mechanism into a longitudinal force to create the relative tension force that will separate the core wire 26 from the stylet wire 24.

Figure 8:
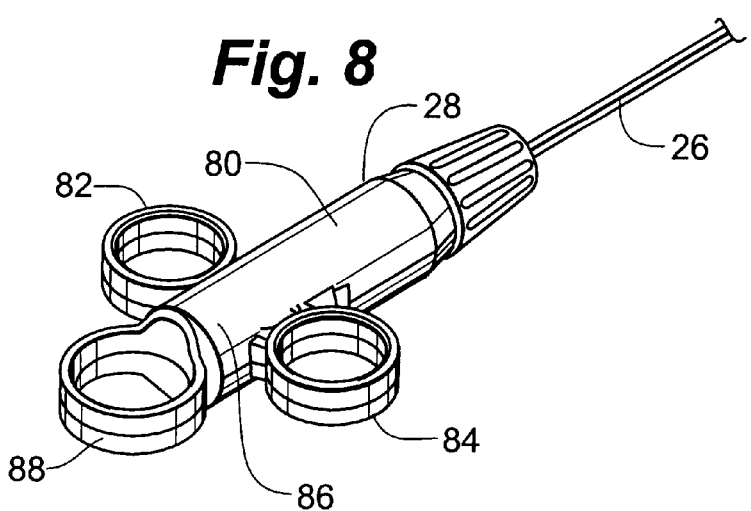
FIG. 8 is a perspective view of an additional embodiment of the manipulative handle of the present invention in which the manipulation is controlled by pulling or pushing the thumb hold of a three-finger handle.
Figure 9:
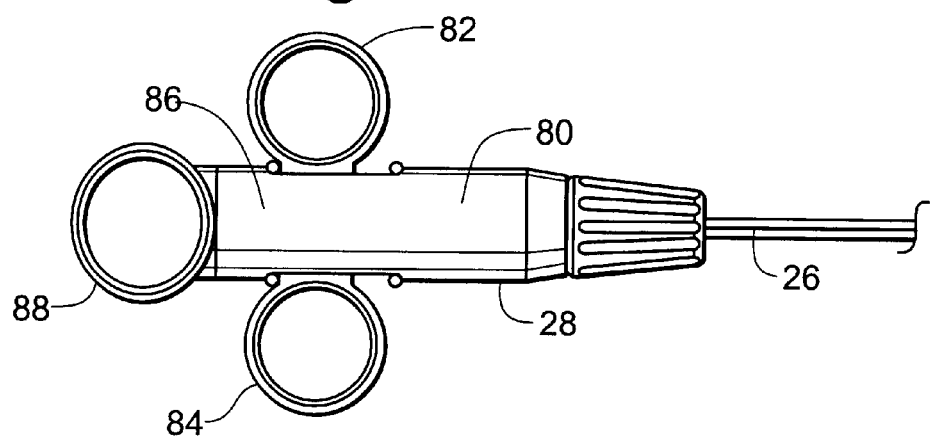
FIG. 9 is a top view of the embodiment shown in FIG. 8.
Figure 10:
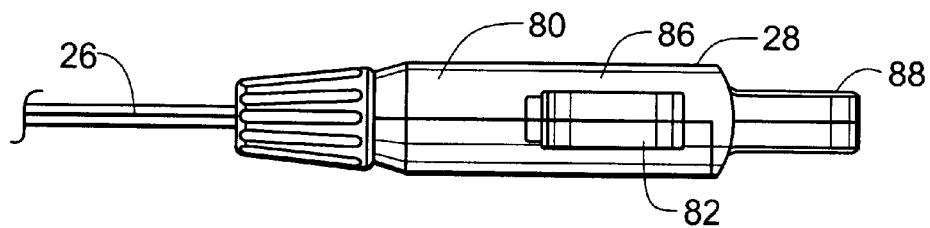
FIG. 10 is a side view of the embodiment shown in FIG. 8.

FIGS. 8, 9, and 10 show a perspective, top, and side view, respectively, of yet another embodiment of the manipulative handle 28 of the present invention. The relative tension force is applied to the core wire 26 by pulling or pushing a pair of finger holds 82 and 84 in relation to the manipulative handle housing 80. The finger holds 82 and 84 are positioned on opposite sides of a middle portion 86 of the housing 80 which preferably includes an additional thumb hold 88 that is not moveable so as to allow for single handed operation of the steerable stylet 20.

Figure 11:
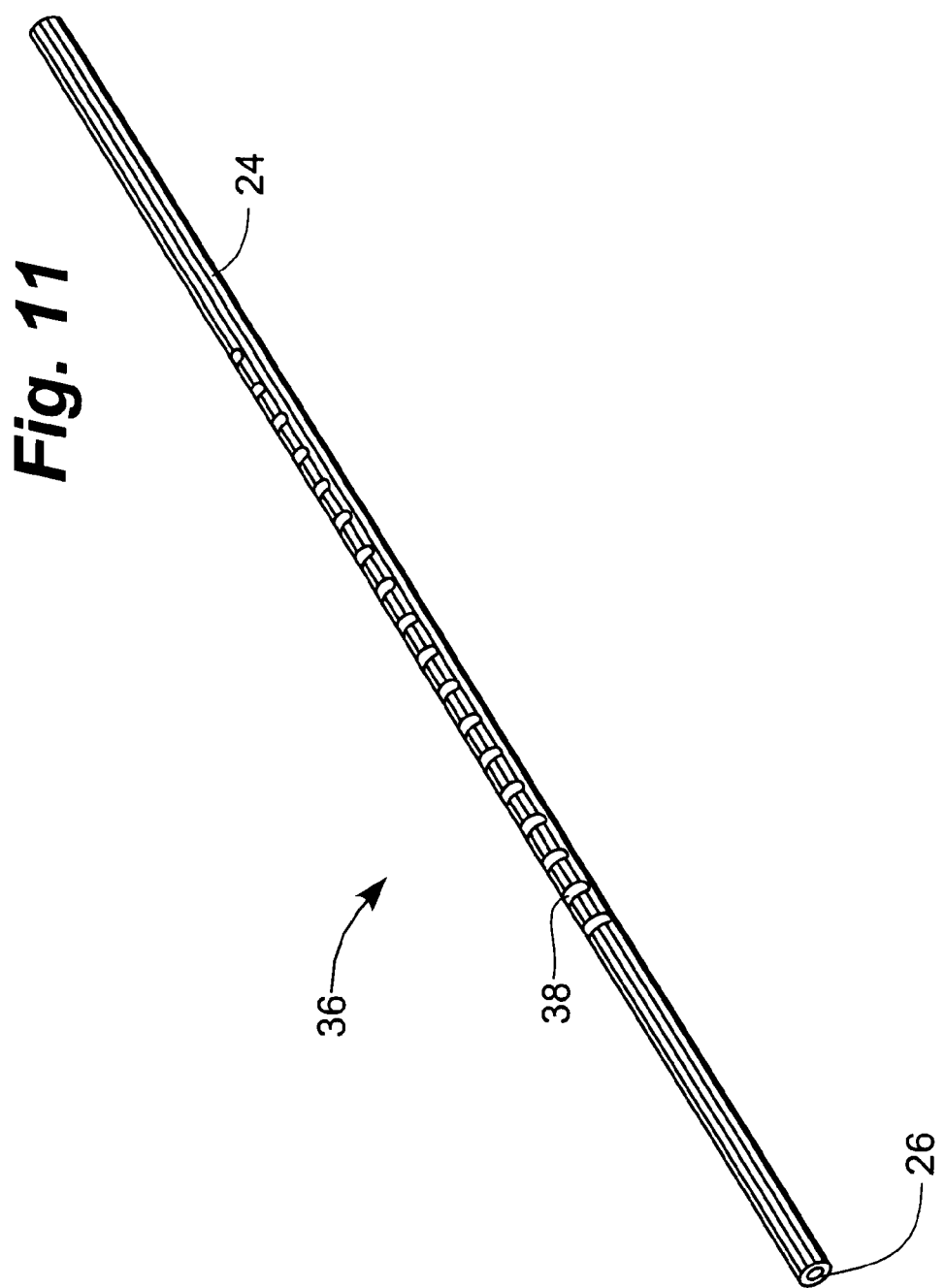
FIG. 11 is a perspective view of an embodiment the distal portion of the stylet wire of the present invention illustrating an arrangement of notches in the stylet wire.

Turning to FIGS. 11 and 12, they illustrate the notches 48 in the distal region 36 of the stylet wire 24. The notches 48 alter the strength of the wall of the stylet wire 24 in the distal region 36 that allows the stylet wire 24 to more easily bend when the relative tension force is applied between the stylet wire 24 and the core wire 26. Preferably, notches or slots 48 are created by an electrical discharge machine (EDM) process. Alternatively, the notches 48 may be created by cutting, laser, or water processes to remove the desired material of the stylet wire from the notches 48. The shape of the notches 48 is preferably a rounded bottom channel, although other shapes such as a V-shape or a rectangular shape are also contemplated. In another embodiment, the effect of notches 48 could be achieved by selectively removing portions of material from the wall of stylet wire 24 at the location similar to the locations of notches 48 and replacing the removed material with a softer material. In still another embodiment, additional material could be added to the wall of stylet wire 24 at locations generally radially opposite of the region where a curve is desired to create a radially differential strength in the wall structure of stylet wire 24 that would encourage bending of the stylet wire 24 at that region.

Spacing of the notches 48 will aid in determining the diameter of the J-shape that can be created by the distal region 36 of the stylet wire 24. Notches 48 that are spaced farther apart will create a larger diameter J-shape. Notches 48 that are spaced closer together will create a smaller diameter J-shape. The width of each notch 48 is critical to be able to position the slots closely without over-scoring the back of the tubular stylet wire 24.

In a preferred embodiment, the stylet wire 24 includes a series of at least ten notches 48 defined along the distal region 36 of the stylet wire 24. In one embodiment, at least a portion of the notches 48 have a progressively decreasing depth distally to proximally along the series as shown best in FIG. 12. Preferably, the portion of the notches 48 that have a progressively decreasing depth is between 5% and 50% of said series and will depend upon the desired application for the steerable stylet 20 and the particular J-shape configuration to be obtained by operation of the steerable stylet 20. Preferably, at least three of the most proximal notches of the series have a progressively decreasing depth with a constant decrease in depth between adjacent notches. In one embodiment, the portion of the notches 48 having a progressively decreasing depth has a constant decrease in depth between adjacent notches. In a preferred embodiment, this constant decrease is 20% between adjacent notches. In an alternative embodiment, the progressively decreasing depths are not constant and may be selected along with alternate spacings between the notches 48 to achieve alternate shapes of the distal end other than a simple J-shape.

Preferably, the distal region 36 is defined beginning between 0.050 inches and 1.000 inches proximal to the distal end of the stylet wire 24 and includes at least twenty notches 48 of between 0.005 inches and 0.015 inches longitudinal width. A spacing between adjacent notches is between 0.010 inches and 0.050 inches. A depth of at least ten of the most distal notches 48 of the series is preferably approximately equal to a radius of the stylet wire 24 minus a wall thickness of the stylet wire. It has been found that this depth provides for maximum bending stiffness in this application.

Figure 22:
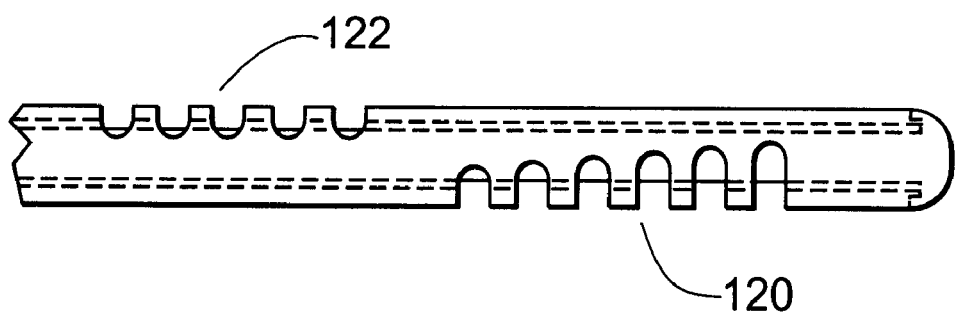
FIGS. 22 and 23 are detailed cross-sectional views of an alternate embodiment of the stylet assembly for creating compound and sigmoidal curves.
Figure 23:
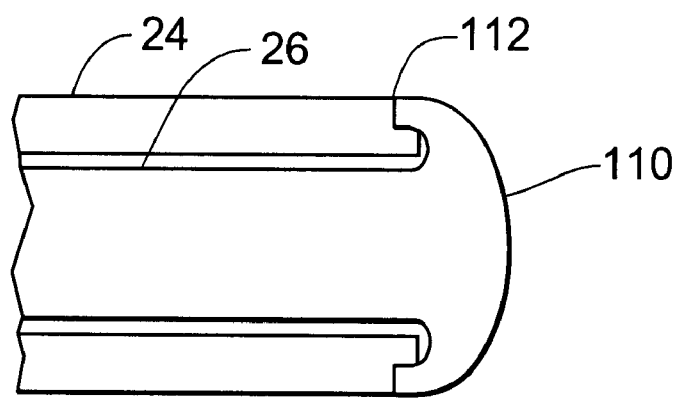

In another embodiment as shown in FIGS. 22 and 23, a stylet assembly particularly adapted for neurological uses is presented. In another embodiment, a longitudinal tip of distal end portion 40 of core wire 26 includes a bulbous tip portion 110 having an outer diameter similar to the outer diameter of stylet wire 24 that extends beyond distal end portion 36 of stylet wire 24. In this embodiment, chamfers 112 are created at the opening of the distal end portion 36 of stylet wire 24 to seat the tip portion 110 of the core wire 26 in the opening and preferably an adhesive, such as an ultraviolet cured adhesive or an acrylate adhesive or the like, is used to secure the two wires together. In a preferred embodiment, the stylet wire is a tubular wire having an outer diameter of 0.013 inches and an inner diameter of 0.008 inches. The core wire 26 is created by starting with a solid core wire of 0.013 inches and center grinding the wire to an outer diameter of 0.007 inches except for the tip portion 110, which remains at an outer diameter of 0.013 inches and is preferably rounded on the exterior. In this embodiment, a polymer sheath is not utilized to keep the outer diameter as small as possible. It will be understood that the selection on inner and outer diameters of the stylet wire 24 are critical in being able to maintain the desired beam strength and that these selections will depend upon numerous factors, including the materials used for both the stylet wire and the core wire, and the nature and character of any notches 48 to be defined in the stylet wire. This embodiment includes 28 total notches 48 spaced at 0.030" with the first notch located 0.035" from the distal end portion 36 of the stylet wire 24. Preferably, the stylet assembly 22 of this embodiment is capable of deflecting at least 45 degrees and preferably up to 90 degrees in response to a relative tension force of about 8 lbs when deflected in a urethane lead.

In this embodiment, the stylet wire 24 can include two or more series of notches 48 that are created in the distal region 36 as shown, for example at 120 and 122. Preferably, each series of notches is spaced apart by at least 0.1 inches. The spacing and dimension of the notches 48 in first series 120 located more distally and the second series 122 located more proximally are chosen in this example to cause the stylet assembly 22 to first bend proximate the first series 120 in response to relative tension between the core wire 26 and the stylet wire 24 and then make a second bend proximate the second series 122 in response to a further increase in the relative tension. In this way, sigmoidal and compound curves can be created. Additionally, by altering the radial orientation of the notches 48 as shown in FIG. 22, it is possible to create sigmoidal and compound curves in different planes. These features are very desirable for many neurological applications where the vascularture is more tortuous than in cardiac applications.

Figure 24:
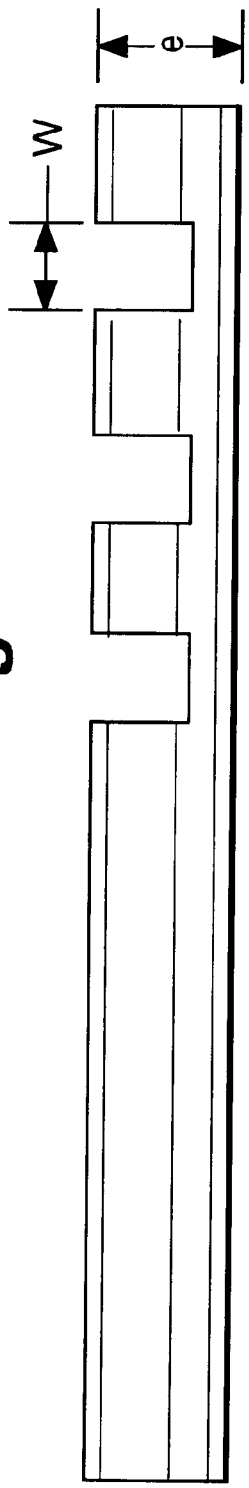
FIGS. 24 and 25 are side and end views of the notches in a distal portion of the stylet assembly.
Figure 25:
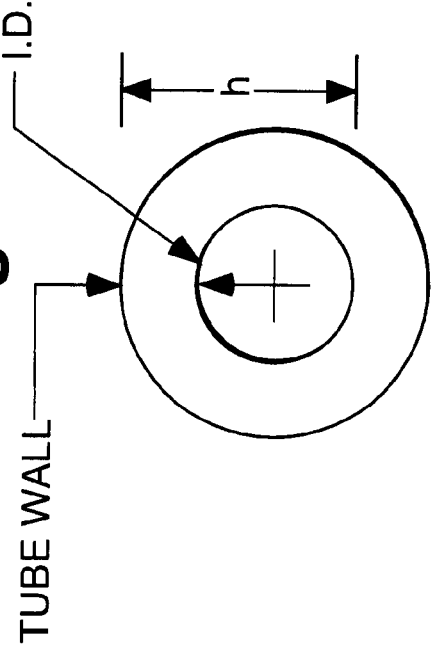

Referring to FIGS. 24 and 25, the calculations for creating the notches 48 of a preferred embodiment will be described. For notches 48 of maximum depth, the cuts should be made to a depth that is equal to the thickness of the wall of stylet wire 24 and preferably the wall thickness ranges between 0.003 and 0.006 inches and the corresponding inner diameter ranges between 0.004 and 0.010 inches.

Referring to FIGS. 24 and 25, the calculations for determining the depth and distribution of notches 48 of a preferred embodiment will be described. For maximum curvature of the stylet wire 24, the cuts should be made to a depth equal to the thickness of the wall of the stylet wire and preferably the wall thickness ranges between 0.003 and 0.006 inches and the corresponding inner diameter ranges between 0.004 and 0.010 inches. The number of notches 48 determines the maximum angle of deflection of the stylet wire 24. The width of the notches 48 determines the maximum amount of bending of the stylet wire 24.

A critical property of solid bodies and areas is the moment of inertia. Moments of inertia are used in calculating the strength of beams, such as the stylet wire 24 of the present invention. Formulas are derived by multiplying basic particles of mass or area by the squares of their respective distances from the reference axis. Therefore, moments of inertia are dependent upon the location of their axis. Moments of inertia of plane area, where I is in the plane of the area are derived from equations for calculating deflective stresses in beams. These formulas have been employed to design the stylet to deflect to the desired positions while maintaining, but not exceeding the maximum allowable stresses under this desired deflection.

The following equations are used to determine the moments of inertia that, in turn, are used to determine the beam strength of the stylet wire 24:

$$A = \frac{Ro^2}{2}(2\alpha - \sin 2\alpha) \qquad \text{(eq. 1)}$$

$$I_x = \frac{ARo^2}{4}\left[1 + \frac{2\sin^3\alpha\cos\alpha}{\alpha - \sin\alpha\cos\alpha}\right] \qquad \text{(eq. 2)}$$

$$I_y = \frac{ARo^2}{4}\left[1 - \frac{2}{3}\left(\frac{\sin^3\alpha\cos\alpha}{\alpha\sin\alpha\cos\alpha}\right)\right] \qquad \text{(eq. 3)}$$

Where $I_x$ and $I_y$ represent the moments of inertia in the x and y planes; A represents the cross sectional area of the stylet wire 24 at the cut; Ro represents the outside diameter of the stylet wire; r represents the inside diameter of the stylet wire; α represents the angle formed between the two radii extending from the center of the stylet wire to the edge of the cut.

As many different embodiments of the present invention can be made without departing from the spirit and scope thereof, it is to be understood that the invention is not limited to the specific embodiments thereof except as defined in the following claims.

What is claimed:

1. A steerable stylet for use within a lumen of an intravascular device comprising:
   a stylet assembly having a distal end portion and a proximal end portion, said stylet assembly including:
      a stylet wire having a lumen defined therein, said stylet wire having an outer diameter of less than 0.016 inches and a beam strength of at least 0.005 lbf as measured by the ASTM E855-90 3-point bend test; and
      a core wire positioned within said lumen of said stylet wire and having a distal end portion of said core wire operably secured to said stylet wire proximate a distal end portion of said stylet wire; and
   a handle proximate said proximal end portion of said stylet assembly, said handle including:
      a hand-held housing structure operably connected to one of a proximal end portion of said stylet wire and a proximal end portion of said core wire;
      an adjustable tensioner mechanism operably connected to the other of said proximal end portion of said stylet wire and said proximal end portion of said core wire to adjust a relative tension force applied between said stylet wire and said core wire; and
      a tension limiter operably arranged to limit said tension force applied between said core wire and said stylet wire to a limit force that is less than a breaking stress force of said stylet wire when said stylet assembly is positioned within said lumen of said intravascular device.

2. The steerable stylet of claim 1 wherein said breaking stress force of said stylet wire is at least six pounds and said limit force of said tension limiter is less than four pounds.

3. The steerable stylet of claim 1 wherein said adjustable tensioner mechanism operably engages with a separate compressible member to increase a force opposing movement of said adjustable tensioner mechanism so as to provide tactile feedback to an operator that is generally indicative of said relative tension force.

4. The steerable stylet of claim 1 wherein said beam strength of said stylet wire is sufficient to cause said stylet wire to return to at least an original position of said stylet wire as said relative tension force is removed from said stylet wire.

5. The steerable stylet of claim 1 wherein said stylet wire includes a series of at least ten notches defined along a distal region of said stylet wire.

6. The steerable stylet of claim 5 wherein said series of a least ten notches includes at least a portion of said notches having a progressively decreasing depth distally to proximally along said series.

7. The steerable stylet of claim 6 wherein said portion of said notches having said progressively decreasing depth comprises between five percent and fifty percent of said series.

8. The steerable stylet of claim 6 wherein each of said notches in said portion of said notches having said progressively decreasing depth has a constant decrease in depth between adjacent notches.

9. The steerable stylet of claim 5 wherein said distal region is defined beginning between 0.050 inches and 1.000 inches proximal to said distal end of said stylet wire and includes at least twenty notches of between 0.005 inches and 0.015 inches longitudinal width with a spacing between adjacent notches of between 0.010 inches and 0.050 inches and a depth of at least ten of the most distal notches of said series being approximately equal to a radius of said stylet wire minus a wall thickness of said stylet wire.

10. The steerable stylet of claim 5 wherein at least three of the most proximal notches of said series have a progressively decreasing depth with a constant decrease in depth between adjacent notches.

11. The steerable stylet of claim 1 wherein said stylet wire includes a plurality of separate sets of notches defined along a distal region of said stylet wire.

12. The steerable stylet of claim 11 wherein each set of notches is spaced apart from one another by at least 0.1 inches and each set of notches includes at least a plurality of notches having a longitudinal width of between 0.005 inches and 0.015 inches with a spacing between adjacent notches of between 0.010 inches and 0.050 inches.

13. The steerable stylet of claim 11 wherein at least one of said sets of notches includes at least a portion of said notches having a progressively decreasing depth distally to proximally along said series.

14. The steerable stylet of claim 11 wherein at least two of said sets of notches have different radial orientations of said notches such that the stylet assembly creates curves in two separate planes in response to said relative tension force.

15. The steerable stylet of claim 11 wherein at least two of said sets of notches have different spacings and widths of said notches such that the stylet assembly creates curves at two different times in response to said relative tension force.

16. The steerable stylet of claim 1 wherein said proximal end portion of said core wire is fixedly connected to said housing structure, said proximal end portion of said stylet wire is fixedly connected to said adjustable tensioner mechanism and said tension limiter has a first end portion fixedly connected to said housing structure and a second end portion operably connected to said adjustable tensioner mechanism.

17. The steerable stylet of claim 16 wherein said tension limiter is comprised of a constant force spring with a maximum tensile retention force less than the breaking stress force of said stylet wire.

18. The steerable stylet of claim 1 wherein said tension limiter is comprised of a spring with a maximum compressive retention force less than the breaking stress force of said stylet wire.

19. The steerable stylet of claim 1 wherein said tension limiter is comprised of an elastomer with a maximum compressive retention force less than the breaking stress force of said stylet wire.

20. The steerable stylet of claim 1 wherein said distal end portion of said core wire is operably secured to said distal end portion of said stylet wire without annealing either of said distal end portions.

21. A steerable stylet for use within a lumen of an intravascular device comprising:
   a stylet wire having a distal end portion, a proximal end portion and a lumen defined in said stylet wire, said stylet wire having an outer diameter of less than 0.016 inches and a beam strength of at least 0.005 lbf as measured by the ASTM E855-90 3-point bend test;
   a core wire having a distal end portion and a proximal end portion, said core wire positioned within said lumen of said stylet wire and having said distal end portion of said core wire operably secured to said stylet wire proximate said distal end portion of said stylet wire; and a handle proximate said proximal end portion of said stylet wire, said handle including a hand-held housing structure having:
  means for adjusting a relative tension force applied between said stylet wire and said core wire; and
  means for limiting said relative tension force to a limit force that is less than a breaking stress force of said stylet wire when said stylet wire is positioned within said lumen of said intravascular device.

22. The steerable stylet of claim 21 wherein said breaking stress force of said stylet wire is at least six pounds and said limit force of said tension limiter is less than four pounds.

23. The steerable stylet of claim 21 wherein said handle further includes means for providing tactile psuedo-feedback to an operator that is generally indicative of said relative tension force.

24. The steerable stylet of claim 21 wherein said beam strength of said stylet wire is sufficient to cause said stylet wire to return to at least an original position of said stylet wire as said relative tension force is removed from said stylet wire.

25. The steerable stylet of claim 21 wherein said stylet wire includes at least one means for altering a wall strength of said stylet wire along a distal region of said stylet wire.

26. The steerable stylet of claim 25 wherein said means for altering the wall strength creates a radially differential wall strength between generally opposing walls of said stylet wire.

27. The steerable stylet of claim 25 wherein said means for altering the wall strength is selected from the set consisting of: means for removing material at a series of locations along said stylet wire, means for adding material at a series of locations along said stylet wire, or any combination thereof.

28. The steerable stylet of claim 25 wherein said means for altering the wall strength comprises a series of means for altering a material characteristic of a wall of said stylet wire located along a portion of said stylet wire.

29. The steerable stylet of claim 28 wherein each of said means for altering a material characteristic of said wall in said portion have differing characteristics between adjacent means.

30. The steerable stylet of claim 28 comprising a plurality of said means for altering the wall strength, each said means for altering the wall strength being spaced apart from one another by at least 0.1 inches.

31. The steerable stylet of claim 30 wherein at least two of said means for altering the wall strength have different radial orientations of said series of means for altering the material characteristic such that the stylet assembly creates curves in two separate planes in response to said relative tension force.

32. The steerable stylet of claim 30 wherein at least two of said series of means for altering the material characteristic have different spacings and widths such that the stylet assembly creates curves at two different times in response to said relative tension force.

33. The steerable stylet of claim 21 wherein said distal end portion of said core wire is operably secured to said distal end portion of said stylet wire by means for adhering without annealing either of said distal end portions.

34. A method of steering a stylet within a lumen of an intravascular device comprising:

providing a steerable stylet including:
  a stylet assembly having a distal end portion and a proximal end portion, said stylet assembly including a stylet wire having a lumen defined therein, said stylet wire having an outer diameter of less than 0.016 inches and a beam strength of at least 0.005 lbf as measured by the ASTM E855-90 3-point bend test, and a core wire positioned within said lumen of said stylet wire and having a distal end portion of said core wire operably secured to said stylet wire proximate a distal end portion of said stylet wire; and
  a handle operably connected to said stylet wire proximate said proximal end portion of said stylet assembly, said handle including a hand-held housing structure, a tension adjuster and a tension limiter;
inserting at least a portion of said stylet assembly into said lumen of said intravascular device; and
selectively deflecting a distal end portion of said intravascular device by using said tension adjuster to adjust a relative tension force applied between said stylet wire and said core wire in such a manner that said tension limiter limits said relative tension force to a limit force that is less than a breaking stress force of said stylet wire.

35. The method of claim 34 wherein the step of selectively deflecting deflects said distal end portion of said intravascular device to a maximum deflection of at least 180 degrees from an original position of said distal end portion of said intravascular device at a bend radius of less than an inch.

36. The method of claim 34 wherein the step of selectively deflecting deflects said distal end portion of said intravascular device to a maximum deflection of at least 45 degrees from an original position of said distal end portion of said intravascular device at a bend radius of less than an inch.

37. The method of claim 34 further comprising:
returning said distal end portion of said intravascular device to at least an original position of said distal end portion of said intravascular device by releasing said relative tension force applied between said stylet wire and said core wire and using said beam strength of said stylet wire to cause said stylet wire to return to a position beyond an original position of said stylet wire.

38. The method of claim 34 wherein said step of selectively deflecting is repeated at least fifty times without inducing stress or fatigue failure in said stylet wire.

39. The method of claim 34 wherein said stylet assembly includes a plurality of regions along said distal end portion having differing wall strengths such that the step of selectively deflecting creates a compound curve of said distal end portion.

40. The method of claim 39 wherein at least two of said plurality of regions are radially offset with respect to each other and the step of selectively deflecting creates curves in at least two different planes.

41. The method of claim 39 where at least two of said plurality of regions having differing characteristics and the step of selectively deflecting creates curves at two different times.

42. A steerable stylet for use within a lumen of an intravascular device comprising:
a stylet assembly having a distal end portion and a proximal end portion, said stylet assembly including:
  a stylet wire having a lumen defined therein, said stylet wire having an outer diameter of less than 0.016 inches and a beam strength of at least 0.005 lbf as measured by the ASTM E855-90 3-point bend test, said stylet wire includes a series of at least ten notches defined along at least one distal region of said stylet wire; and a core wire positioned within said lumen of said stylet wire and having a distal end portion of said core wire operably secured to said stylet wire proximate a distal end portion of said stylet wire; and a handle proximate said proximal end portion of said stylet assembly, said handle including a hand-held housing structure having means for adjusting a relative tension force applied between said stylet wire and said core wire.

43. The steerable stylet of claim 42 wherein said series of a least ten notches includes at least a portion of said notches having a progressively decreasing depth distally to proximally along said series.

44. The steerable stylet of claim 43 wherein said portion of said notches having said progressively decreasing depth comprises between five percent and fifty percent of said series.

45. The steerable stylet of claim 43 wherein each of said notches in said portion of said notches having said progressively decreasing depth has a constant decrease in depth between adjacent notches.

46. The steerable stylet of claim 42 wherein said distal region is defined beginning between 0.050 inches and 1.000 inches proximal to said distal end of said stylet wire and includes at least twenty-five notches of between 0.005 inches and 0.015 inches longitudinal width with a spacing between adjacent notches of between 0.010 inches and 0.050 inches and a depth of at least ten of the most distal notches of said series being approximately equal to a radius of said stylet wire minus a wall thickness of said stylet wire.

47. The steerable stylet of claim 42 wherein at least three of the most proximal notches of said series have a progressively decreasing depth with a constant decrease in depth between adjacent notches.

48. The steerable stylet of claim 42 wherein said stylet wire includes a plurality of separate sets of notches defined along a distal region of said stylet wire.

49. The steerable stylet of claim 48 wherein each set of notches is spaced apart from one another by at least 0.1 inches and each set of notches includes at least a plurality of notches having a longitudinal width of between 0.005 inches and 0.015 inches with a spacing between adjacent notches of between 0.010 inches and 0.050 inches.

50. The steerable stylet of claim 48 wherein at least one of said sets of notches includes at least a portion of said notches having a progressively decreasing depth distally to proximally along said series.

51. The steerable stylet of claim 48 wherein at least two of said sets of notches have different radial orientations of said notches such that the stylet assembly creates curves in two separate planes in response to said relative tension force.

52. The steerable stylet of claim 48 wherein at least two of said sets of notches have different spacings and widths of said notches such that the stylet assembly creates curves at two different times in response to said relative tension force.

53. The steerable stylet of claim 42 wherein said distal end portion of said core wire is operably secured to said distal end portion of said stylet wire without annealing either of said distal end portions.

54. A steerable stylet for use within a lumen of an intravascular device comprising:

a stylet assembly having a distal end portion and a proximal end portion, said stylet assembly including:

a stylet wire having a lumen defined therein, said stylet wire having an outer diameter of less than 0.016 inches and a beam strength of at least 0.005 lbf as measured by the ASTM E855-90 3-point bend test, said stylet wire includes a series of means for altering a material characteristic of a wall of said stylet wire located along a portion of said stylet wire; and a core wire positioned within said lumen of said stylet wire and having a distal end portion of said core wire operably secured to said stylet wire proximate a distal end portion of said stylet wire; and a handle proximate said proximal end portion of said stylet assembly, said handle including a hand-held housing structure having means for adjusting a relative tension force applied between said stylet wire and said core wire.

55. The steerable stylet of claim 54 wherein each of said means for altering a material characteristic of said wall in said portion have differing characteristics between adjacent means.

56. The steerable stylet of claim 54 comprising a plurality of said series of means, each of said series of means being spaced apart from one another by at least 0.1 inches.

57. The steerable stylet of claim 56 wherein at least two of said series of means have different radial orientations such that the stylet assembly creates curves in two separate planes in response to said relative tension force.

58. The steerable stylet of claim 56 wherein at least two of said series of means have different characteristics such that the stylet assembly creates curves at two different times in response to said relative tension force.

59. The steerable stylet of claim 54 wherein said distal end portion of said core wire is operably secured to said distal end portion of said stylet wire by means for adhering without annealing either of said distal end portions.

* * * * *